US009381251B2

(12) United States Patent
Borros Gomez et al.

(10) Patent No.: US 9,381,251 B2
(45) Date of Patent: *Jul. 5, 2016

(54) THERMOPLASTIC PASTE FOR REPAIRING LIVING TISSUES

(71) Applicants: INSTITUT QUIMIC DE SARRIA CETS, FUNDACIO PRIVADA, Barcelona (ES); UNIVERSITAT RAMON LLULL, FUNDACIO PRIVADA, Barcelona (ES)

(72) Inventors: Salvador Borros Gomez, Barcelona (ES); David Horna Tomas, Barcelona (ES)

(73) Assignees: INSTITUT QUIMIC DE SARRIA CETS, FUNDACIO PRIVADA, Barcelona (ES); UNIVERSITAT RAMON LLULL, FUNDACIO PRIVADA, Barcelona (ES)

(*) Notice: Subject to any disclaimer, the term of this patent is extended or adjusted under 35 U.S.C. 154(b) by 0 days.

This patent is subject to a terminal disclaimer.

(21) Appl. No.: 14/174,442

(22) Filed: Feb. 6, 2014

(65) Prior Publication Data

US 2014/0155267 A1 Jun. 5, 2014

Related U.S. Application Data

(63) Continuation of application No. 12/993,985, filed as application No. PCT/ES2009/070143 on May 6, 2009, now Pat. No. 8,703,111.

(30) Foreign Application Priority Data

May 23, 2008 (ES) .................................. 200801532

(51) Int. Cl.
| | |
|---|---|
| *A61K 47/34* | (2006.01) |
| *A01N 59/20* | (2006.01) |
| *C08G 63/80* | (2006.01) |
| *C08L 67/02* | (2006.01) |
| *A61L 27/44* | (2006.01) |
| *C08K 3/22* | (2006.01) |
| *C08K 3/38* | (2006.01) |
| *C08K 3/40* | (2006.01) |
| *A01N 25/02* | (2006.01) |
| *A61K 33/42* | (2006.01) |
| *C08K 3/30* | (2006.01) |
| *C08K 3/32* | (2006.01) |

(52) U.S. Cl.
CPC ............... *A61K 47/34* (2013.01); *A01N 25/02* (2013.01); *A01N 59/20* (2013.01); *A61K 33/42* (2013.01); *A61L 27/44* (2013.01); *C08K 3/22* (2013.01); *C08K 3/38* (2013.01); *C08K 3/40* (2013.01); *C08K 3/30* (2013.01); *C08K 2003/325* (2013.01)

(58) Field of Classification Search
CPC ........ A61L 27/44; A01N 25/02; A01N 59/20; A61K 33/42; A61K 47/34; C08K 2003/325; C08K 3/22; C08K 3/30; C08K 3/38; C08K 3/40
See application file for complete search history.

(56) References Cited

U.S. PATENT DOCUMENTS

| | | | |
|---|---|---|---|
| 6,730,721 B2 | 5/2004 | Bezemer et al. | |
| 8,703,111 B2 * | 4/2014 | Borros Gomez et al. | .. 424/78.08 |
| 2003/0086958 A1 | 5/2003 | Arnold et al. | |
| 2006/0099876 A1 | 5/2006 | Buckley et al. | |
| 2006/0199876 A1 | 9/2006 | Troczynski | |
| 2007/0224245 A1 | 9/2007 | Ameer | |
| 2011/0130290 A1 | 6/2011 | Borros Gomez et al. | |

FOREIGN PATENT DOCUMENTS

| | | |
|---|---|---|
| EP | 1902738 A2 | 3/2008 |
| WO | 9961518 A1 | 12/1999 |
| WO | 0050559 A1 | 10/2000 |
| WO | 0059559 A1 | 10/2000 |
| WO | 0110478 A1 | 2/2001 |
| WO | 03026714 A1 | 4/2003 |
| WO | 2005041656 A2 | 5/2005 |
| WO | 2005051446 A1 | 6/2005 |
| WO | 2006133134 A2 | 12/2006 |
| WO | 2007092559 A2 | 8/2007 |
| WO | 2008036206 A2 | 3/2008 |

OTHER PUBLICATIONS

Dar, Encyclopedia of Chemical Processing, 2007, Block Copolymers Chapter, pp. 1-14.*
Partial Translation of Notice of Grounds for Rejection; Japanese Patent Application No. 2011-510011 listing the Search Report of Prior Art Documents dated Aug. 29, 2014. 1 page.
JP2007046050 A; published Feb. 22, 2007; Abstract only; 1 page.
Arens, M.; Hydroxyl number—Collective Works of DGF, Report 116: German standard methods for the study of fats, fat products, surfactants and related substances, Report 88: Analysis of fats XXVII, Fat science Technology, Year 92, No. 9, pp. 371-373\, (1990).
Balakrishnan, "Self-cross-linking biopolymers as injectable in situ forming biodegradable scaffolds", Biomaterials 26 (2005) 3941-3951.
Ding, Tao, "Synthesis, characterization and in vitro degradation study of a novel and rapidly degradable elastomer" Polymer Degradation and Stability 91 (2006) 733-739.

(Continued)

*Primary Examiner* — Abigail Fisher
(74) *Attorney, Agent, or Firm* — Dunlap Codding, P.C.

(57) ABSTRACT

This invention relates to a thermoplastic paste with a highly thixotropic rheology, the components of which are a block biopolymer and a bioceramic. The material described herein can be used in bone implants and in the regeneration of both animal and plant live tissues.

22 Claims, 3 Drawing Sheets

(56) References Cited

OTHER PUBLICATIONS

Hedberg, Elizabeth L., "In vitro degradation of porous poly(propylene fumarate)/poly(DL-lactic-co-glycolic acid) composite scaffolds", Biomaterials 26 (2005) 3215-3225.

Jeong, Byeongmoon, "Thermogelling Biodegradable Polymers with Hydrophilic Backbones: PEG-g-PLGA", Macromolecules 2000, 33, 8317-8322.

Kylma, Janne, "Synthesis and Characterization of a Biodegradable Thermoplastic Poly(ester-urethane) Elastomer", Macromolecules 1997, 30, 2876-2882.

Saad, Gamal R., "Synthesis and Thermal Properties of Biodegradable Poly(ester-urethane)s Based on Chemo-Synthetic Poly[(R,S)-3-hydroxybutyrate]", Macromol. Biosci. 1, pp. 91-99, 2001.

Shikanov, Ariella, "Poly(sebacic acid-co-ricinoleic acid) Biodegradable Injectable in Situ Gelling Polymer" Biomacromolecules 2006, 7, 288-296.

Wang, Yadong, "A tough biodegradeable elastomer" Research Article: Nature Publishing Group hhttp://biotech.nature.com, pp. 602-606, 2002.

Yang, Jlan, "Synthesis and evaluation of poly(diol citrate) biodegradable elastomers", Biomaterials 27 (2006) 1889-1898.

EP Search Report; Application 09749962.8-1455 / 2301593 PCT/ES20090770143; May 13, 2013; 3 pages.

* cited by examiner

THERMOPLASTIC PASTE FOR REPAIRING LIVING TISSUES

CROSS REFERENCED TO RELATED APPLICATIONS

This application is a continuation of U.S. application Ser. No. 12/993,985 filed on Jan. 5, 2011 as the U.S. National Phase of PCT International Patent Application No. PCT/ES2009/070143 filed on May 6, 2009, which claims priority to Spanish Patent Application No. P200801532 filed on May 23, 2008, all of these applications are herein incorporated by reference in their entirety.

TECHNICAL FIELD

The present invention is comprised within the field of biocompatible materials, especially those which are used in tissue engineering for repairing live tissues. The present invention particularly belongs to the field of thixotropic biomaterials, to the processes for obtaining them, and to their uses in the treatment for repairing, regenerating and conditioning live tissues.

BACKGROUND

Biocompatible materials or biomaterials are inert compounds designed to be implanted or incorporated within a live system for the purpose of replacing and/or regenerating live tissues and their functions. Various biomaterials which promote cell proliferation, support physiological loads and are easy to handle and synthesize have been developed in tissue engineering (Biomaterials 27 (2006) 1889-1898; Biomaterials 26 (2005) 3215-322). Among these materials there are various types of biocompatible polymers which, furthermore, are often biodegradable (Nature Biotechnology, Volume 20, June 2002 (602-606); Macromolecules 1997, 30, 2876-2882; Macromol. Biosci. 2001, 1, 91-99; Polymer Degradation and Stability 91 (2006) 733-739). Some materials have a low viscosity under synthesis conditions but are capable of polymerizing and forming gels under physiological conditions, which allows them to be injectable and prevents the need for surgery (Biomacromolecules 2006, 7, 288-296; Biomaterials 26 (2005) 3941-3951). There are abundant examples and combinations in the scientific literature. By way of a sample, Byeongmoon et al. (Macromolecules 33, 8317-8322, 2000) describe the synthesis of a block biopolymer which is biodegradable because it contains organic acids such as lactic acid and glycolic acid and biopolymers such as polyethylene glycol capable of gelling under physiological conditions without causing tissue irritation and which are furthermore biodegradable and resorbable by the organism. However, the materials of this type cannot support physiological loads because they lack hardness, therefore they are mechanically ineffective when they are used in load structures such as bones in animals or branches in plants. Furthermore, some polymers experience deformations when they are exposed to high temperatures or to stress for a prolonged time period and experience a deterioration which is so fast that it sometimes does not allow the complete repair of the structure before the degradation of the polymer. To solve this problem, a series of composite materials using bioceramics have been designed in the field of the art. The ceramics increase the hardness and reduce the rate of degradation of the polymer. It is generally desirable for the bioceramic particles to be homogeneously distributed in the biodegradable polymer so that the properties of the compound are also homogeneous. Some medical implants of structural elements of the body, such as bones, are occasionally manufactured with a polymer/ceramic composite material. International patent application WO-2008036206-A1 describes an implantable composite material of biopolymer and bioceramic, which facilitates the resistance and reduces the wear of the implant. Unlike injectable polymers, these implants are normally formed outside the body and are placed by means of surgery. Unfortunately, such implants have problems of adaptation to the target surfaces, which are normally irregular, have cracks or a non-standard morphology.

In certain types of injuries, a treatment strategy in which the implant is a platform for the reconstruction of the tissue is possible. Various patent applications are known in the state of the art which describe the preparation of platforms with very diverse features. A critical problem for the correct operation of these platforms is their correct adjustment to the irregularities of the structure to be treated. However, once molded, these compounds cannot be remodeled either in order to be accurately adjusted to the surface to be repaired. International patent application WO-2007092559-A1 describes a composite material of bioceramic and biodegradable biopolymers suitable for bone implants. The composition of the composite material described therein provides it with a suitable rigidity for physiological loads but prevents the correct adaptation to the surface to be repaired.

The inventors of the present application have surprisingly discovered that a material made up of a bioceramic and a block polymer formed by rigid blocks alternated with flexible blocks, such as polyethylene glycol polymers for example, allows remodeling after the hardening of the platform. A platform with an initial morphology which can be remodeled by means of mechanical forces when implanting it for its perfect adaptation to the surface to be repaired can thus be created. This material can furthermore be applied in fields other than the biomedicine field, for example in tissue engineering of plants, as a platform for grafts or as a rooting inducer.

BRIEF SUMMARY

Figure 1:
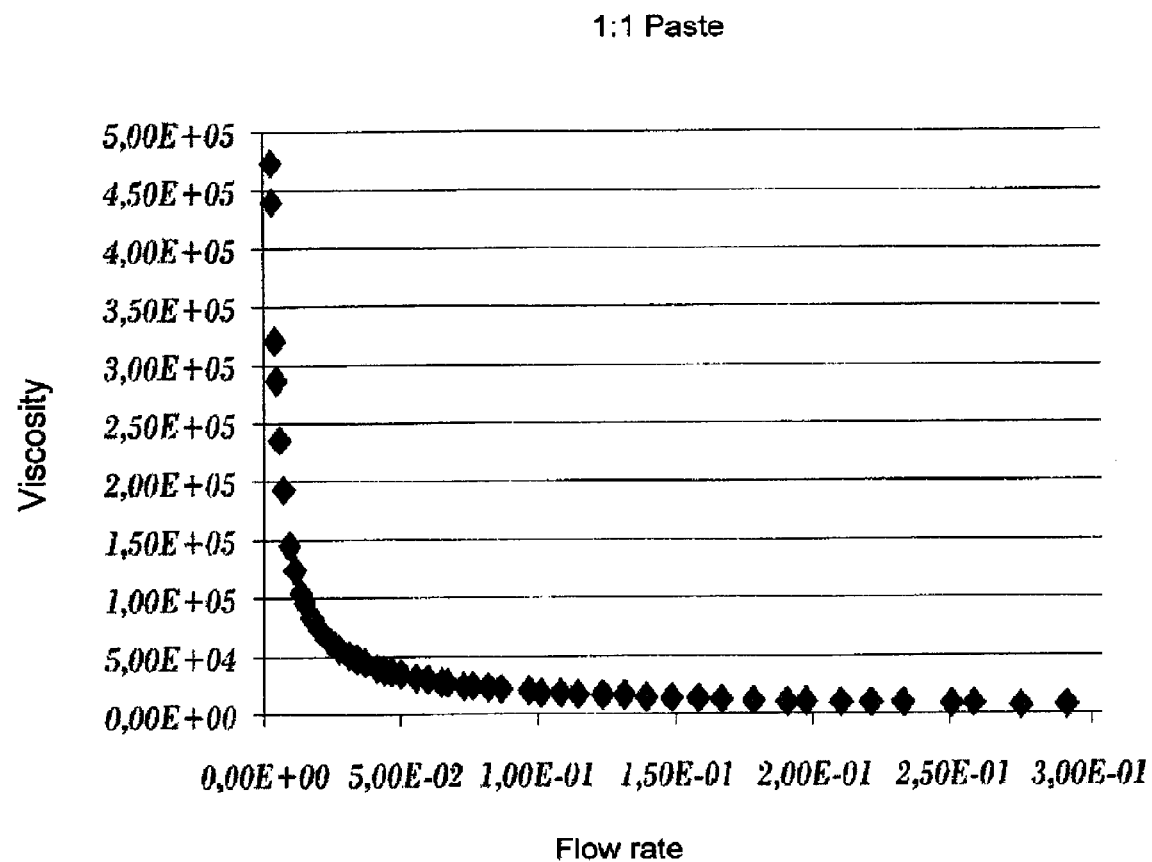
FIG. 1 is a graph showing the highly thixotropic rheology of the thermoplastic paste of the invention. The study shown herein was conducted at a temperature of 36° C. As can be observed the viscosity at a stress of 0 Pa is 4.75 E+05 Pa·s.

A first object of the present invention relates to a composite material, with a thixotropic rheology, which in an initial state has a paste consistency and a thermoplastic nature and is mainly formed by a block biopolymer and a bioceramic which constitutes between 10-70% of the total weight of the material. The block biopolymer corresponds to the general formula $[(A\text{-}B\text{-}C)_n\text{-}D\text{-}E\text{-}D\text{-}(A\text{-}B\text{-}C)_n\text{-}]_m$, wherein A and C are dihydroxy or diamino monomers, B and D are dicarboxylic acids, E is a polymer with a hydroxyl number $\geq 10$ and n and m are numerical indices $\geq 1$. This block biopolymer comprises a rigid block $(A\text{-}B\text{-}C)_n$ and a flexible block $(\text{-}D\text{-}E\text{-}D\text{-})$. The rigid block consists of a polymer mostly formed by ester type bonds and optionally including amide type bonds, whereas the flexible block consists of a second polymer comprising a hydrocarbon chain containing ester or ether bonds.

A second object of the present invention is a process for preparing the material of the present invention by means of microwaves, which comprises a first step of synthesis in a microwave of the co-polymer block (A-B-C)$_n$, wherein A is a linear aliphatic dihydroxy monomer or a diamine, B is a dicarboxylic acid and n is a numerical index ≥1; a second step of synthesis in a microwave of the copolymer block -D-E-D-, wherein D is a dicarboxylic acid and E is a polymer with a hydroxyl number ≥10; a third step of elongation in a microwave of the copolymer block (A-B-C)$_n$ with the copolymer block -D-E-D-, to create the block polymer and a last step of mixing of the block polymer with the bioceramic.

A third object of the present invention comprises the use of the material of the present invention in the treatment for repairing live tissues, both animal and plant tissues such as for example bone, skin, hair, nails and hooves, superficial wounds and cuts, coupling of agricultural grafts or stimulation of plant rooting.

The following definitions are provided to facilitate the understanding of the specification and the claims:

Thermoplastic paste is a composition of a composite material, which is a solid formed by materials having different physical characteristics in which each of the materials retains its own identity while it provides certain properties to the composite. Thermoplastic paste especially relates herein to a deformable material capable of hardening at temperatures of between 20-50° C. and softening by mechanical action or by heat; which has a strong thixotropic nature and the constituent materials of which comprise, in a non-limiting manner, ceramic particles and a block polymer, with a hard block and another flexible block including a polymer with a hydroxyl number ≥10, with a high molecular weight and formed by chains capable of associating by means of weak forces.

A block polymer is a copolymer formed by distinguishable groups or blocks of macromolecules with different repetition numbers.

A biopolymer is a polymer used in applied biology, which is compatible with the organism in which it is housed; especially a non-allergenic polymer. Biopolymers comprise both natural polymeric macromolecules, either isolated from organisms or produced by means of molecular biology or genetic engineering techniques, and synthetic polymeric macromolecules which are known or designed ad hoc. Both can comprise homopolymers, copolymers or a mixture thereof.

A bioceramic is a material which is used in applied biology. It is crystalline or amorphous, essentially inorganic, non-metallic, porous and brittle; which is formed and matured by the action of heat. It can be inert or active and take part in biological processes. It can remain invariable, be reabsorbed or dissolved.

Thixotropy is the property of some fluids which show a change in viscosity dependent on external forces such as heat or friction such that in the absence of said external forces, the viscosity of the fluid is low or very low whereas after the application of said forces, the viscosity of the fluid increases temporarily.

The hydroxyl number relates to the amount of OH groups which in a polymer are capable of forming polyester and polyether bonds. The oxygens of this type of bond are capable of forming hydrogen bonds with a ceramic forming part of the same composite material as said polymer. Thus, the lower the hydroxyl number, the higher the number of possible hydrogen bonds between the polymer and the ceramic. The hydroxyl number is the number of mg of potassium hydroxide equivalent to the hydroxyl groups in one gram of material. The hydroxyl groups are acetylated with a known amount of acetic anhydride. The excess of anhydride is subsequently decomposed by means of adding water and the acetic acid formed is titrated with a 0.5 N ethanolic potassium hydroxide solution. The methodology described in *Fat and Science Technology*, 1989. no. 9-1990, pp. 371-373 is followed to calculate the hydroxyl number. The hydroxyl number is calculated according to the formula:

$$OH = \frac{(V_2 - V_1) \cdot N \cdot 56, 1}{m} + AV$$

wherein $V_1$ is the volume in ml of the potassium hydroxide solution necessary for the sample; $V_2$ is the volume in ml of the potassium hydroxide solution necessary for the blank; N is the normality of the potassium hydroxide solution; m is the weight of the polymer in grams and AV is the acid value of the sample.

In the present invention the term "resorbable" relates to the fact that the support disappears over time as it is replaced by regenerated tissue. In the present invention "assimilable" relates to the fact that the components of the paste can be integrated in the normal structures of the organism without needing to be previously degraded. In the present invention "degradable" relates to the fact that the organism can decompose the elements forming the material by means of enzymatic processes to incorporate them in their normal biochemical processes.

DETAILED DESCRIPTION

In a first aspect, the object of the present invention relates to a composite material the rheology of which is characteristically thixotropic, therefore after hardening it is capable of recovering certain viscosity depending on the mechanical and heat forces applied. The constituent elements of the composite material, which is referred to hereinafter as thermoplastic paste, mainly consist of a block polymer and a bioceramic and optionally other minor components. The composition of the block polymer is particularly important for the adaptability of the thermoplastic paste since it is the alternation of rigid blocks with flexible blocks which allows the thixotropic rheology. Thus, the flexible blocks initially establish associations by means of weak forces with the bioceramic. In the paste at rest, when it is sufficiently cooled, this association is uncoupled, the paste being cohered by associations between the rigid block and the bioceramic as well as by means of H bonds between the polymer chains such that, when mechanical forces and a small amount of heat are applied on the rigid paste (the hardness of which comes from the bioceramic), the flexible block again establishes the weak forces with the bioceramic with the consequent increase of the viscosity and resulting in the thixotropic rheology described in FIG. 1. The study of FIG. 1 was conducted at 36° C. therefore it is demonstrated that, under physiological conditions, the thermoplastic paste meets the necessary hardness requirements for replacing and regenerating tissues such as bone, the function of which is developed at similar temperatures.

Figure 2:
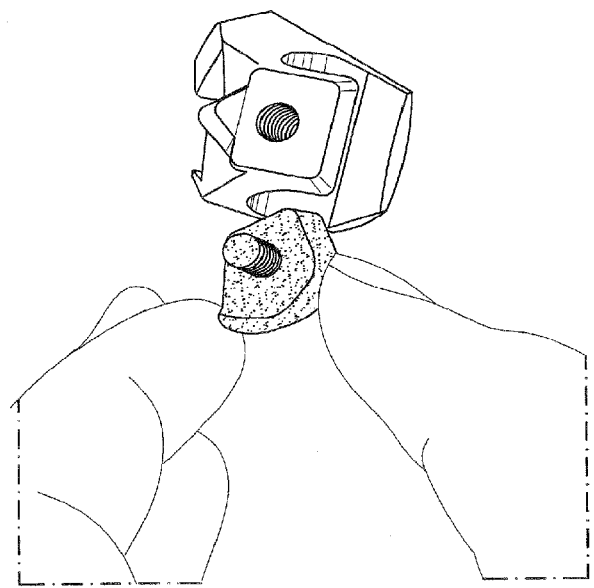
FIG. 2 is a demonstration of the adaptability of the paste of the invention to irregular surfaces. It can be seen that, by means of mechanical forces, a ball of thermoplastic paste adapts to the irregular surface of the figure.
Figure 2:
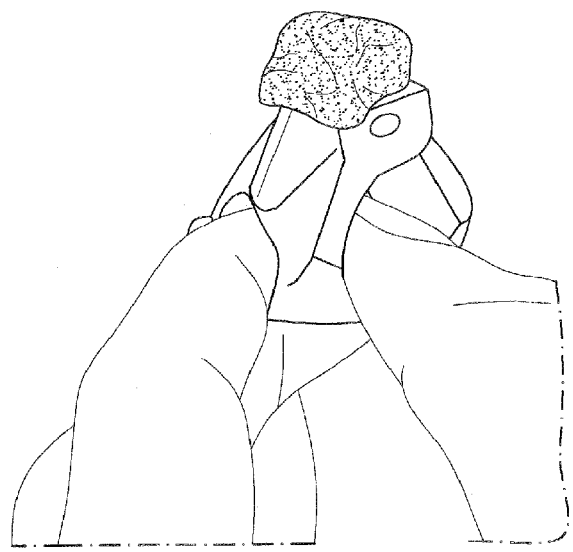
Figure 2:
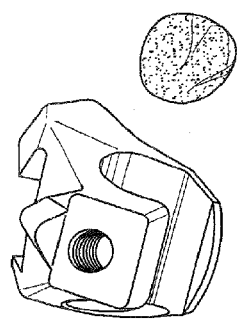

As has been explained above, the thixotropic rheology is the main feature of the present invention. This main feature of the invention confers the advantage of allowing a perfect adaptation to the surface of the tissue to be treated. The elements conferring this advantage provide the material with the appearance and the consistency of a paste which can be molded by the action of mechanical and heat forces. FIG. 2 demonstrates the perfecta adaptability of the paste to irregular surfaces. Another characteristic advantage of the present invention is its biocompatibility. The thermoplastic paste of the present invention is biocompatible because it is well tolerated by the organism into which it is incorporated. This advantage is given by the nature of its components: the block biopolymer is made up of made up of two types of polymers, rigid and flexible, both of them being degradable, resorbable and assimilable by living organisms. Likewise, the bioceramic is also resorbable, assimilable and biodegradable.

In one embodiment, the biopolymer forming the rigid block is a heteropolymer made up of glutamic acid and a diol of no more than 10 carbons, for example 1,8-octanediol. In alternative embodiments, caprolactone, lactic acid, glycolic acid, fumaric acid monomers and mixtures thereof can also be used. Any monomer which is considered suitable for the function of this block within the composite material can be introduced in the block. In a particular embodiment, the rigid block of the block biopolymer comprises amide type bonds in a percentage less than or equal to 5% of the total weight of the paste. The result obtained would thus be a higher rigidity of the material which experiences a certain reduction of its thixotropic nature.

In another particular embodiment, the polymer E is chosen from the group of ethylene oxides, polyamidoamines, polyamines, polyols and combinations thereof. In a preferred embodiment, the flexible block is formed by ethylene oxide polymers, preferably polyethylene glycol (PEG), the molecular weight of which does not exceed 20,000 kDa. In another preferred embodiment, the ethylene oxide polymer contains up to 50 branches.

The thermoplastic paste can house any biopolymer with a sufficient number of free hydroxyl radicals, such that the latter are capable of forming hydrogen bonds with the ceramic. For example, in another embodiment, the flexible block is a biopolymer of the glycosaminoglycan (GAG) family, such as hyaluronic acid. When the paste of the present invention contains hyaluronic acid, it is highly compatible with the nervous, epithelial and connective tissue. Thus, in another particular embodiment, the polymer E is a glycosaminoglycan selected from the group consisting of chondroitin sulfate, dermatan sulfate, keratan sulfate, heparin, heparan sulfate, hyaluronic acid and mixtures thereof.

In the present invention, it is preferable for the bioceramic component to be particulate and be homogeneously distributed in the ultrastructure of the paste. The more uniform the distribution of the bioceramic particles, the more uniform the properties of the material and the more predictable its behavior in each practical application. In the present invention, the bioceramic materials include in a non-limiting manner the ceramics of calcium phosphate, aluminium oxide, zirconium oxide, silicon oxide, pyrolytic carbon, bioglass, salts of copper, iron, cobalt, zinc, magnesium, manganese, calcium, boron, titanium dioxide and combinations thereof. In a preferred embodiment, the bioceramic is hydroxyapatite. Hydroxyapatite is the mineral component of natural bone and will be included in the present invention when the latter is used in the treatment for repairing bone structures. In another preferred embodiment, the bioceramic component comprises bioglass. Bioglass is a highly biocompatible non-crystalline ceramic. Bioglass can be substituted with another amorphous ceramic with equivalent properties or with another highly biocompatible amorphous solid. Some of the embodiments of the present invention are designed for their use in the field of agriculture and industrial or ornamental gardening. A particular embodiment of the present invention would incorporate copper (II) salts in the bioceramic as an antifungal agent for the application thereof in the assembly of plant grafts.

Without modifying the essential components of the present invention, varied elements can be included in the thermoplastic paste in percentages such that, without significantly affecting the rheology of the material, they confer to it specific properties for its application in different practical uses. In a particular embodiment, the present invention comprises, in addition to the block biopolymer and the bioceramic, a third component in a percentage by weight 1% to be chosen from antibiotics, animal or plant growth factors, cell factors, rooting factors, flowering promoting factors, fruit ripening factors, ripening inhibition factors, senescence factors, germination factors, etc. They could include animal or plant hormones, alkaloids, nutritional elements, oils, cosmetic conditioners and combinations thereof. Optionally, the invention also contemplates seeding the material of the invention with prokaryotic or eukaryotic cells.

Figure 3:
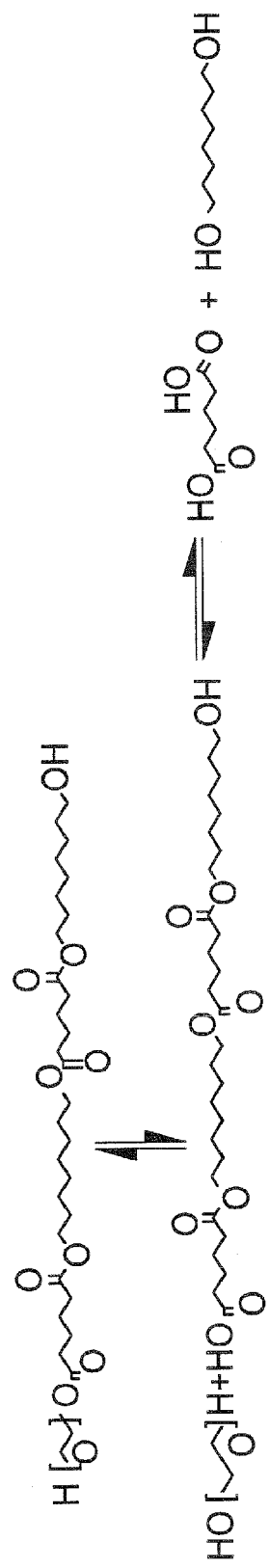
FIG. 3 shows the steps of synthesis of the block polymer of the material of the invention.

In a second aspect, the present invention relates to a process of synthesis by means of microwaves which, compared to the conventional synthesis, confers the advantage of obtaining a faster rate of reaction given by the electromagnetic forces conferred to it by the microwaves, in addition to preventing the thermal mismatches associated with the conduction and/or the temperature. Shorter reaction times in addition to milder temperatures are thus achieved. The synthesis of polymers by means of microwaves occurs in the range of minutes whereas by conventional methods the process would last for hours. To synthesize the composite material of the invention, in a first step the carboxylic acid and the diol are reacted such that the carboxylic acid is located at the ends of the chains since the carboxylic groups must be at the ends of the rigid block so that they can react with the flexible block. Once the rigid block has thus been obtained, the second step is performed in which it is reacted with the flexible block; once the base polymer has been obtained, it is mixed with the ceramic of choice. During the steps of synthesis, it is convenient to inject compressed air for ventilating, increasing the microwave effect and favoring polymerization. The synthesis of the polymers can likewise be performed by means of conventional processes. This would require higher temperatures and it would furthermore be necessary to choose suitable catalysts and a system for removing the water produced in the polycondensation. FIG. 3 illustrates the reactions taking place in the synthesis by means of microwaves of the thermoplastic paste of the present invention.

In a third aspect, the object of the present invention relates to the use of the thermoplastic paste in the treatment for repairing both animal and plant live tissues. In a preferred embodiment, the animal tissue is mammalian bone, including human bone. In this case, the paste of the present invention would include a bioceramic such as for example hydroxyapatite, which is the mineral component of natural bone, to stimulate the regeneration of the bone. Other bioceramics with equivalent or improved properties could likewise be included for this particular use of the thermoplastic paste of the present invention. In a more preferred embodiment, the thermoplastic paste thus formed is used in the treatment of bone diseases and fractures.

In another preferred embodiment, the thermoplastic paste is used in the treatment and conditioning of surface structures such as skin, hair, nails and hooves as well as in the treatment of superficial wounds and cuts. In this case, the thermoplastic paste of the present invention includes a polymer E promoting cell proliferation and migration, such as hyaluronic acid, for example. Also, for example, cytotoxic effectors for the treatment of injuries caused by a disproportionate cell growth such as tumors, for example. Regardless of the polymer of choice for the flexible block, minor constituents will be included in the paste to achieve suitable therapeutic or cosmetic effects for each case. They can include, as has been stated above, cytotoxic compounds, cell differentiation or growth factors, antiviral, antibiotic and antifungal compounds, particles carrying nucleic acids intended to modify the cell expression of tissue intrinsic or extrinsic genetic elements, nutritional elements and conditioners such as cosmetic oils and combinations of all of them.

In another particular embodiment, the thermoplastic paste is used in the treatment for repairing plant tissues, such as lignified plant tissues for example. In a preferred embodiment, the present invention is used in the coupling of agricultural grafts. In this case, the thermoplastic paste of the present invention includes a bioceramic comprising copper (II) salts, which act like an antifungal agent. Furthermore or alternatively, the thermoplastic paste of the present invention can include other components with equivalent or improved features for this same purpose, either as major components forming part of the essential components or as minor components in a proportion not greater than 1%. Another preferred embodiment of the present invention comprises the use of the described thermoplastic paste in the stimulation of plant rooting of, for example, bushes and trees. In this case, the thermoplastic paste of the present invention includes among its minor components plant hormones and optionally prokaryotic cells for the purpose of stimulating the normal physiological processes of such tissues. For the same purpose, other components of equivalent or improved features can be included in the paste of the present invention.

EXAMPLES

Example 1

Synthesis of the Thermoplastic Paste

Reagents:

12 g of glutaric acid (0.09 moles) and 11.1 g of 1,8-octanediol (0.08 moles) are reacted in a microwave oven (Discovery CEM) at a power of 100 W for 1 hour. The work is performed under vacuum (100 mbar) and cooling the system with compressed air to maintain the temperature constant at 120° C. A rigid block is thus generated.

The rigid block is subsequently reacted with 2000 polyethylene glycol (6.5 g, 3 mM) in the same microwave reactor for 240 minutes and at a power of 100 W a 120° C. The work is again performed under vacuum and with cooling with compressed air.

The resulting polymer (block biopolymer) (10 g) is mixed with 10 g of low crystallinity hydroxyapatite obtained in the laboratory of the inventors by means of a sol-gel process (E. Garreta 2005, doctoral dissertation, Institut Quimic de Sarrià-Universitat Ramon Llull) by means of a Speed Mixer® type planetary mixer.

Example 2

Use of the Paste with Hydroxyapatite in Bone Repair

Using the polymer synthesized by the method of Example 1, a thermoplastic paste is obtained upon mixing at 1:1 ratios by weight with hydroxyapatite, achieving a moldable and adaptable paste.

This paste is implanted in calvarial defects in rats. No signs of inflammation in the specimens have been observed in the preliminary observations. The defect is observed as completely covered after three months.

Example 3

Use of the Paste with Copper Sulfate in the Coupling of Plant Grafts

The thermoplastic polymer of the invention the method of synthesis of which is described in Example 1 is mixed at a 1:0.02 ratio of copper sulfate, a product with a high fungicidal activity. The resulting easy-to-apply paste is deposited on recently pruned fruit tree branches. After the application, a homogeneous coating on the wound which is mechanically stable is observed. After two months no residue is observed on the already recovered wound and the appearance of fungi and any other disease related to the pruning process are not observed either.

The invention claimed is:

1. Thermoplastic paste with thixotropic rheology comprising:
   a) block biopolymer, of formula $[A\text{-}B\text{-}C)_n\text{-}D\text{-}E\text{-}D(A\text{-}B\text{-}C)_n\text{-}]_m$, comprising a rigid block $(A\text{-}B\text{-}C)_n$ and a flexible block $(\text{-}D\text{-}E\text{-}D\text{-})$,
      wherein:
         A and C are dihydroxy or diamino monomers,
         B and D are dicarboxylic acids,
         E is a polymer with a hydroxyl number $\geq 10$,
         n is a numerical index $\geq 1$, and
         m is a numerical index $> 1$,
      and wherein:
         the rigid block, $(A\text{-}B\text{-}C)_n$ consists of a polymer comprising ester type bonds and optionally amide type bonds and,
         wherein the flexible block, $(\text{-}D\text{-}E\text{-}D\text{-})$, consists of a second polymer comprising a hydrocarbon chain containing ester or ether type bonds,
   b) bioceramic in a proportion of 10-70% of the total weight of the thermoplastic paste.

2. Thermoplastic paste according to claim 1, comprising diamino monomers in the rigid polymer in a proportion 5% of the total weight of the thermoplastic paste.

3. Thermoplastic paste according to claim 1, wherein E is a polymer to be chosen from the group of ethylene oxide polymers, polyamidoamines, polyamines, polyols and combinations thereof.

4. Thermoplastic paste according to claim 3, wherein the biopolymer E is an ethylene oxide polymer with a molecular weight between 500-20000 kDa.

5. Thermoplastic paste according to claim 4, wherein the biopolymer E is an ethylene oxide polymer with a molecular weight between 1500-10000 kDa.

6. Thermoplastic paste according to claim 5, wherein the biopolymer E is an ethylene oxide polymer with a molecular weight between 2000-3000 kDa.

7. Thermoplastic paste according to claim 3, wherein the biopolymer E is an ethylene oxide polymer containing between 3-50 branches.

8. Thermoplastic paste according to claim 1, wherein the biopolymer E is a glycosaminoglycan selected from the group consisting of chondroitin sulfate, dermatan sulfate, keratin sulfate, heparin, heparin sulfate, hyaluronic acid and mixtures thereof.

9. Thermoplastic paste according to claim 1, wherein the bioceramic is selected from the group of ceramics of calcium phosphate, aluminum oxide, zirconium oxide, silicon oxide, pyrolytic carbon, bioglass, salts of copper, iron, cobalt, zinc, manganese, magnesium, calcium, boron, titanium dioxide and combinations thereof.

10. Thermoplastic paste according to claim 9, wherein the bioceramic is hydroxyapatite.

11. Thermoplastic paste according to claim 9, wherein the bioceramic comprises copper (II) salts.

12. Thermoplastic paste according to claim 9, wherein the bioceramic comprises bioglass.

13. Thermoplastic paste according to claim 1, furthermore comprising a third component in a percentage by weight ≤1% to be chosen from antibiotics, growth factors, prokaryotic or eukaryotic cells, cell factors, nutritional elements, oils, cosmetic conditioners and combinations thereof.

14. Process for preparing the thermoplastic paste of claim 1, comprising:
   1) synthesis in a microwave of the copolymer block $(A-B-C)_n$ wherein
      A is either a linear aliphatic dihydroxy monomer or a diamine,
      B is a dicarboxylic acid,
      N is a numerical index ≥1,
   2) synthesis in a microwave of the copolymer block -D-E-D- wherein
      D is a dicarboxylic acid,
      E is a polymer with a hydroxyl number ≥10,
   3) Elongation in a microwave of the copolymer block $(A-B-C)_n$ with the copolymer block -D-E-D-, to create the block polymer, and polymerization to create the block copolymer of claim 1, and
   4) Mixing of the block polymer with the ceramic.

15. A method of repairing or conditioning a live tissue comprising implanting into the live tissue a thermoplastic paste according to claim 1, wherein the live tissue is selected from the group consisting of bone, skin, hair, nails, hooves, and plant tissue.

16. The method according to claim 15, wherein the live tissue is a mammalian bone.

17. The method according to claim 15, wherein the live tissue is a plant tissue.

18. The method according to claim 17, wherein the plant tissue is a lignified tissue.

19. A method of treating a bond fracture comprising implanting into the bone the thermoplastic paste according to claim 1.

20. A method of coupling agricultural grafts comprising applying the thermoplastic paste according to claim 11 on the grafts before coupling.

21. A method of stimulation of plant rooting comprising applying the thermoplastic paste according to claim 13 on to roots of a plant.

22. The method according to claim 15, wherein the live tissue is a human bone.

* * * * *